United States Patent [19]

Danby

[11] Patent Number: 5,366,346

[45] Date of Patent: Nov. 22, 1994

[54] ELECTRONICALLY CONTROLLED INTRAVENOUS FLUID INFUSION DEVICE

[75] Inventor: Hal C. Danby, Sudbury, England

[73] Assignee: Danby Medical Limited, Essex, England

[21] Appl. No.: 969,572

[22] Filed: Oct. 30, 1992

[30] Foreign Application Priority Data

Nov. 4, 1991 [GB] United Kingdom ............... 9123325

[51] Int. Cl.$^5$ ............................................. F04B 49/00
[52] U.S. Cl. ........................................... 417/18; 341/35
[58] Field of Search ............... 341/35; 604/65, 66, 604/67; 128/12, 13; 417/18

[56] References Cited

U.S. PATENT DOCUMENTS

| | | | |
|---|---|---|---|
| 3,655,123 | 4/1972 | Judson et al. | 604/67 |
| 4,105,028 | 8/1978 | Sadier et al. | 604/65 |
| 4,261,360 | 4/1981 | Perez | 604/67 |
| 4,275,464 | 6/1981 | Schmidt | |
| 4,976,687 | 12/1990 | Martin | 604/65 |
| 5,061,923 | 10/1991 | Miller et al. | 340/825.31 |
| 5,151,019 | 9/1992 | Danby et al. | 417/474 |

FOREIGN PATENT DOCUMENTS

| | | |
|---|---|---|
| 0049364 | 4/1982 | European Pat. Off. |
| 0050208 | 4/1982 | European Pat. Off. |
| 0109182 | 5/1984 | European Pat. Off. |
| 3214661 | 11/1982 | Germany |
| 2059634 | 4/1981 | United Kingdom |
| 2201948A | 9/1988 | United Kingdom |

Primary Examiner—Richard A. Bertsch
Assistant Examiner—David W. Scheuermann
Attorney, Agent, or Firm—Oblon, Spivak, McClelland, Maier & Neustadt

[57] ABSTRACT

A microprocessor controlled volumetric infusion pump is set as to volume and rate of infusion by two digipots (shaft encoders) each having sixteen detented positioned in 360 degrees. The microprocessor is programmed such that the extent to which the parameter is changed for a given rotation of its setting digipot depends on the speed with which the digipot is rotated. For slow or normal rotation, unit change in parameter is produced for each detented position traversed. Faster rotation causes the setting to jump from one to the next of a series of preselected preferred settings, irrespective of the number of detented positions traversed. The direction of rotation determines whether the setting increases or decreases.

10 Claims, 4 Drawing Sheets

ELECTRONICALLY CONTROLLED INTRAVENOUS FLUID INFUSION DEVICE

FIELD OF THE INVENTION

This invention relates to electronically controlled infusion devices, and more particularly to infusion device which may be set to provide a desired volume of fluid to be infused intravenously at a desired flow rate as dictated by the needs of a patient under treatment.

DISCUSSION OF THE BACKGROUND

Examples of infusion pump arrangements are to be found described in copending commonly owned U.S. patent application Ser. No. 07/430,851, now U.S. Pat. No. 5,151,019 the subject matter of which is incorporated by reference into the present specification.

SUMMARY OF THE INVENTION

As is well-known, medical personnel operate under considerable time pressure and one object of the present invention is to provide an improved infusion control device which may be set to provide required volumes of liquid to be infused and/or rates of flow relatively speedily and in a manner which tends to reflect the sense of urgency with which medical staff operate.

This object and other objects are achieved according to this invention by providing a new and improved electronically controlled infusion device which may be set as to at least one operating parameter by a signal generated by the movement of a control by an operator, the extent of the change in the operating parameter for a given extent of movement of the control being dependant upon the speed with which the control is operated by the operator.

Preferably the device is such that both the volume to be infused and the flow rate are parameters which are set as described above, in which case, normally a dedicated control is provided for each parameter.

Preferably means are provided responsive to two or more rates of movement, normal or slow movement providing incremental change in the setting of the parameter, or respective parameter, and faster movement causing the setting of the parameter to jump from one predetermined preferred setting to another separated therefrom by a plurality of incremental setting changes.

Preferably, the device is such that for setting the flow rate the last mentioned means is responsive to two rates of movement, normal or slow movement and fast movement.

Preferably the device is such that for setting the volume-to-be-infused the last mentioned means is responsive to three rates of movement.

Preferably the device of the invention is such that for setting the volume-to-be-infused the last mentioned means is responsive to three rates of movement, normal or slow movement causing incremental setting changes; fast movement causing the setting to jump to the next multiple of 100 ml of volume of fluid to be infused and very fast movement causing the setting to jump to the next adjacent multiple of 1000 ml of volume-to-infused.

Preferably the movement is a rotary movement and preferably the signal generating control is a digipot or shaft encoder.

BRIEF DESCRIPTION OF THE DRAWINGS

A more complete appreciation of the invention and many of the attendant advantages thereof will be readily obtained as the same becomes better understood by reference to the following detailed description when considered in connection with the accompanying drawings, wherein.

DETAILED DESCRIPTION OF THE PREFERRED EMBODIMENTS

Figure 1:
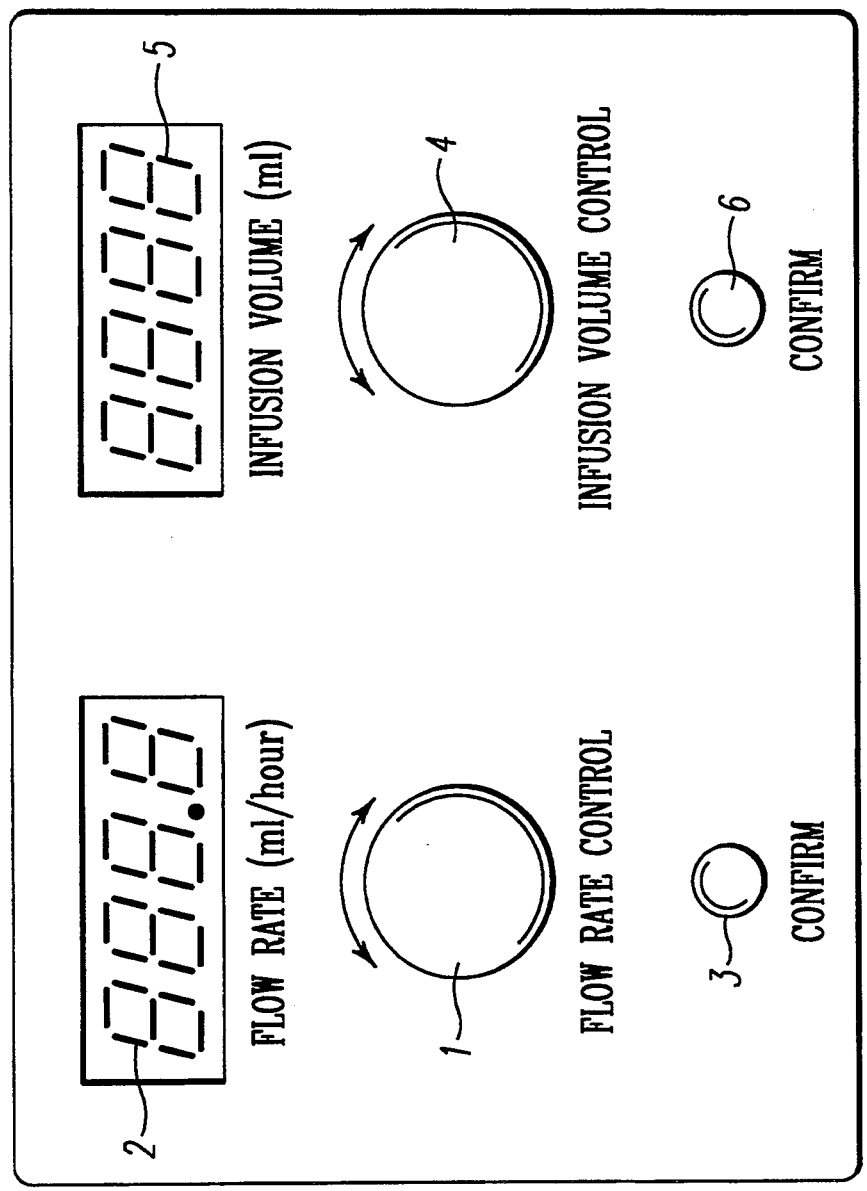
FIG. 1 is a schematic representation of the control panel of one example of electronically controlled volumetric infusion pump arrangement in accordance with the present invention.

Referring now to the drawings, wherein like reference numerals designate identical or corresponding parts throughout the several views, and more particularly to FIG. 1 thereof, the microprocessor controlled pump (not represented) is as described in detail in our U.S. application Ser. No. 07/430,851 now U.S. Pat. No. 5,151,019 to reference may be made for further information.

Setting of the flow rate of the pump is provided for by means of a so-called digipot or shaft encoder 1. A digital display 2 is arranged to indicate the flow rate setting achieved as digipot 1 is rotated clockwise to increase the rate or anti-clockwise to decrease the rate. A "confirm" button 3 is arranged, when pressed, to cause the pump to commence pumping at the selected rate, when a "start" button (not shown) is operated, or to change from a previously selected rate to the selected new rate, as displayed on display 2.

Adjustment of the volume-to-be-infused setting of the pump is provided for by means of another digipot 4. A digital display 5 is arranged to display the volume-to-be-infused setting achieved as digipot 4 is rotated clockwise to increase the volume-to-be-infused or anti-clockwise to decrease the volume-to-be-infused. A "confirm" button 6 is arranged, when pressed, to cause the pump to deliver the selected volume of fluid (at the flow-rate set by digipot 1) when the aforementioned start button is operated. If the pump is already running, operating "confirm" button 6 causes the selected volume-to-be-infused setting to be changed to the new setting, as selected by digipot 4. The control panel illustrated in FIG. 1 typically will be provided with explanatory legends for each control element, as shown in FIG. 1.

Digipots 1 and 4 each have sixteen detented positions in three hundred and sixty degrees. The pump is required to be programmed to provide flow rates of between 0.5 and 999 ml/hr and to deliver volumes of between 1 and 9999 ml. Relying upon a normal change of one digipot position per unit change in flow rate or volume-to-be-infused, sweeping through the whole range in each case would be time consuming in the extreme.

However, the microprocessor is programmed to be responsive to the rate at which pulses are generated by the digipots 1 or 4 such that upon fast rotation the setting of the respective operating parameter (flow rate or volume-to-be-infused, as the case may be) jumps from one predetermined preferred setting to the next (greater or lesser dependant upon the direction of rotation) in a series of preferred settings ("sticky numbers"). From that setting, the respective digipot is rotated again either quickly to jump to the next adjacent predetermined preferred setting or slowly to produce a change of setting unit by unit as the digipot in rotated from detented position to detented position.

For setting the flow rate, the preferred rates between which the settings jump i.e., called "sticky numbers", upon fast rotation of the digipot 1, in ml/hr are:
0.5
5.0
25
41
50
81
100
125 and thereafter in multiples of 100 ml/hr up to the aforementioned 999 ml/hr.

For setting the flow rate, all of the preferred settings have the same priority. For setting the volume-to-be-infused however, it is more likely that multiples of 1000 ml will be selected as the volume required rather than some intermediate value. Taking this into account, in the case of the volume-to-be-infused digipot 4 the microprocessor is programmed to be responsive to a third speed band as follows:

Slow rotation One increment/decrement per digipot detent position.

Fast rotation Jump to next adjacent
larger/smaller multiple of 100 ml for one (or more) digipot detent position.

Very fast rotation (flicking) Change to next adjacent larger/smaller multiple of 1000 ml.

Provided that the number of volume-to-be-infused digipot detent positions traversed does not exceed the number of positions that would be required to be traversed under slow rotation to change from one preferred setting to the next, on fast or very fast (flicking) rotation the number of detent positions traversed is irrelevant.

Figure 2:
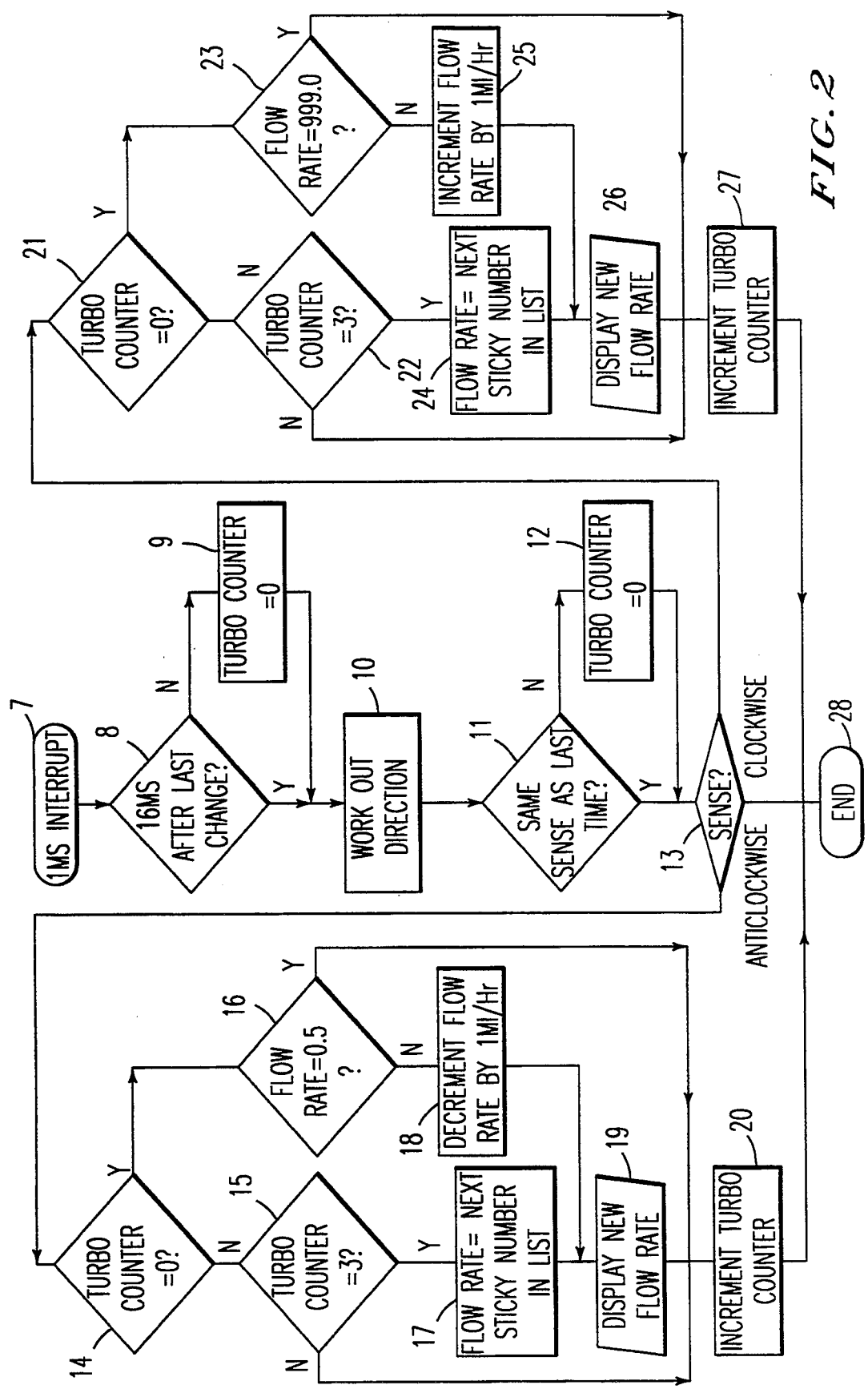
FIG. 2 is a flow chart appertaining to the microprocessor program controlling the flow rate setting of the pump.
Figure 3A:
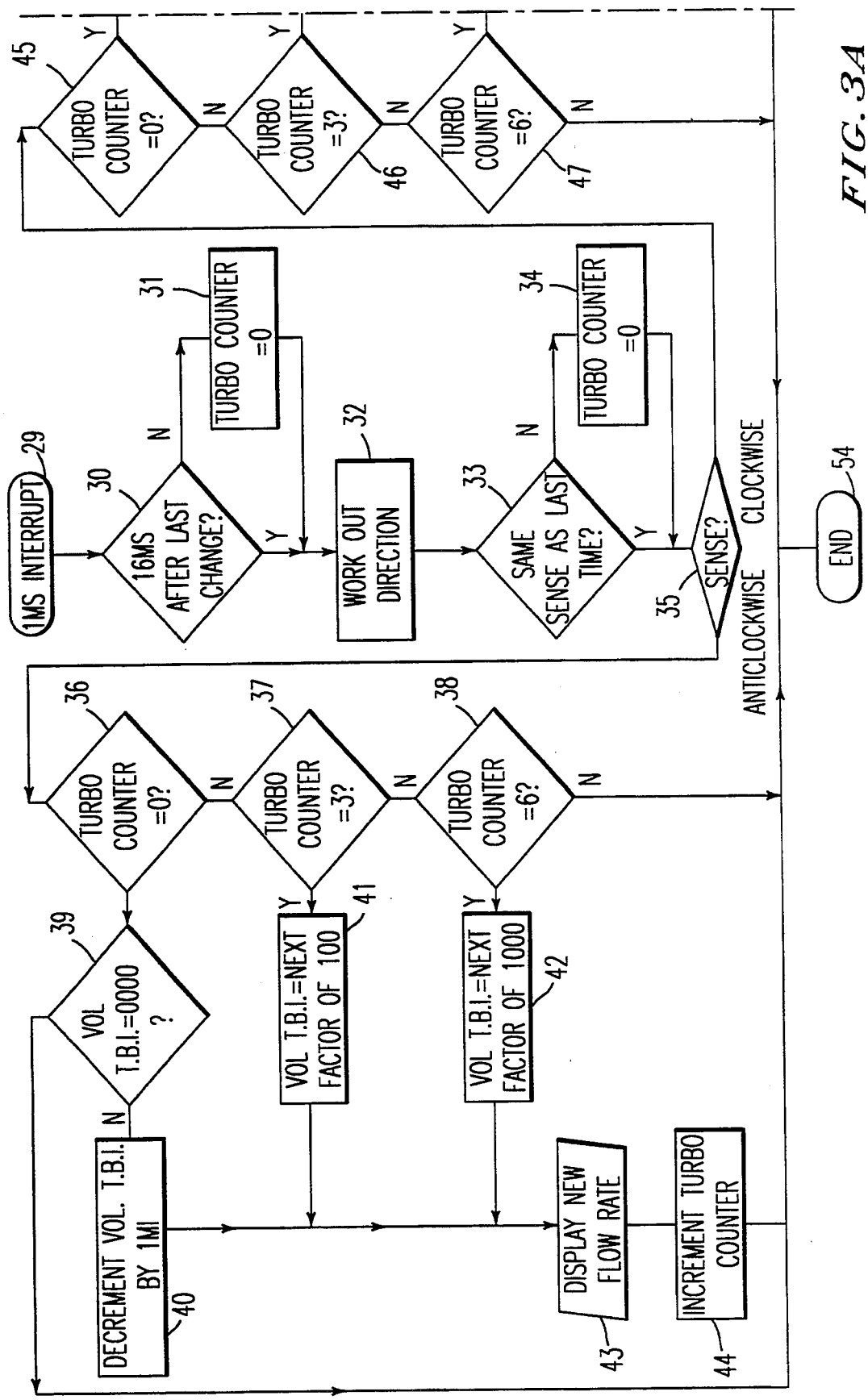
FIG. 3 (A and B) is a flow chart appertaining to the microprocessor program controlling the volume-to-be-infused setting of the pump.
Figure 3B:
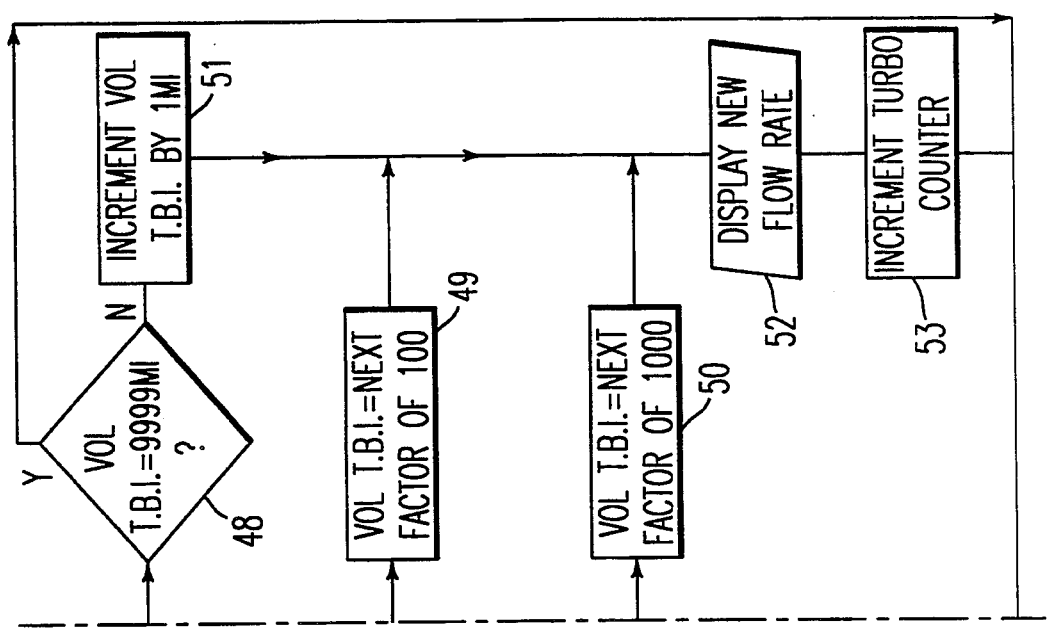

Referring to FIGS. 2 and 3, whilst the programming of the microprocessor will be a matter within the competence of one skilled in the art having regard to the information hereinbefore given, the flow chart of FIG. 2 appertaining to flow rate setting and the flow chart of FIG. 3 appertaining to volume-to-be-infused (Vol t.b.i.) setting may be of assistance in this.

As shown in FIG. 2, processing of the flow rate setting begins with a 1 ms interrupt in step 7, followed by a determination in step 8 as to whether or not 16 ms has elapsed after the last change in the control setting. If not, in step 9 the turbo counter is maintained at a "0" setting, and if so, in step 10 a direction is worked out. The turbo counter (not shown) functions to track how many detents, or "sticky points", have been rotated in a 16 msec time period. In step 11, it is determined whether or not the direction determined in step 10 has the same sense as determined after a previous 1 ms interrupt, and if not, in step 12 the turbo counter is maintained at "0" and if so, processing proceeds to step 13 in which it is determined whether or not rotation of the control is clockwise or anticlockwise or counter clockwise.

If the result of step 13 is a determination that rotation of the control has been in an anticlockwise direction, processing proceeds to step 14 in which it is determined whether or not the turbo counter has a value of "0". If not, it is determined whether or not the turbo counter has a value of "3". If the result of step 15 is "no", processing proceeds to step 20 in which the turbo counter is incremented. If the result of step 15 is "yes", processing proceeds to step 17 in which it is determined that the flow rate is the next sticky number in the list, whereupon this processing continues to step 19, wherein the new flow rate is displayed.

On the other hand, if the result of step 14 is a determination that the value of the turbo counter is equal to "0", processing proceeds to step 16 in which it is determined whether or not the flow rate is equal to 0.5 ml, the lowest flow rate. If "yes", processing proceeds to step 20 and the turbo counter is incremented. If the result of step 16 is "no", the flow rate is decremented by 1 ml in step 18, and in step 19 the new flow rate is displayed. Once again, after display in step 19, the turbo counter is incremented in step 20 and processing is then ended in step 28.

Similar processing is performed if the result of step 13 is a determination that the control has been rotated in a clockwise direction. If so, processing then proceeds to step 21 in which it is determined whether or not the value of the turbo counter equals "0". If "no", processing proceeds to step 22 in which it is determined whether or not the value of the turbo counter equals "3". If "no", processing proceeds to step 27, whereupon the turbo counter is incremented.

On the other hand, if the result of step 21 is a determination that the value of the turbo counter equals "0", processing proceeds to step 23 in which it is determined whether or not the flow rate equals 999.0 ml, the highest flow rate. If "yes", processing proceeds to step 23 and the turbo counter is incremented. If the result of step 23 is "no", the flow rate is incremented by 1 ml/hr in step 25 and the new flow rate is then displayed in step 26, whereupon the turbo counter is incremented in step 27.

If the value of the turbo counter is determined to be equal to "3" in step 22, processing proceeds to step 24 in which it is determined that the flow rate is equal to the next sticky number in the list and then the flow rate is displayed in step 26 and the turbo counter incremented in step 27 followed by proceeding to the end of the interrupt in step 28.

FIG. 3 illustrates the processing steps for determining the volume-to-be-infused setting. Steps 29-35 of FIG. 3 correspond to steps 7-13 in FIG. 2, respectively, and reference is made to the above description for the operations being thereby performed.

If it is determined in step 35 that rotation of the controller was in an anti-clockwise or counterclockwise direction, processing proceeds to step 36 in which it is determined whether or not the value of the turbo counter is zero. If "no" in step 37, it is then determined whether or not the value of the turbo counter equals "3". If "no", it is then determined in step 38 whether or not the value of the turbo counter equals "6". If "no", processing proceeds to the end of the interrupt in step 54.

If on the other hand the result of step 36 is a determination that the value of the turbo counter equals "0", it is determined that the volume t.b.i. equal 0000 in step 39. If "yes", processing proceeds to the end of the interrupt in step 54, and if "no", processing proceeds to step 40 in which the volume t.b.i. is decremented with 1 ml. Thereafter, a new flow rate is displayed in step 43 and the turbo counter incremented in step 44, whereupon the processing proceeds to the end of the interrupt in step 54.

If the result of step 37 is a determination that the turbo counter has a value equal to "0" the volume t.b.i. is determined to be the last factor of 100 and the new flow rate is displayed in step 43, the turbo counter incremented in step 44 and the interrupt ended in step 54.

Similarly, in step 42, it is determined that the volume t.b.i. is equal to the next factor of 1000 and in step 43 the new flow rate is displayed followed by the above-noted processing steps 44 and 54.

If the result of processing step 35 is the determination that the control has been rotated in a clockwise direction, then steps 45, 46 and 47 corresponding to steps 36, 37 and 38 are again performed. If the result of steps 45, 46 and 47 are each "no", the interrupt is ended in step 54. If the result of step 45 is a determination that the turbo counter value equals "0", in step 48 it is determined whether or not the volume t.b.i. equals 999 ml, and if so, the interrupt is ended in step 54. If the result of step 48 is "no", the volume t.b.i. is incremented by 1 ml in step 51 the new volume t.b.i. is displayed in step 52 followed by incrementing of the turbo counter in step 53, and ending of the interrupt in step 54.

If the result of step 46 is "yes", in step 49, it is determined that the volume t.b.i. is the next factor of 100, followed by display of the new volume t.b.i. in step 52, incrementing of the turbo counter in step 53 and ending of the interrupt in step 54. Similarly, if the result of step 47 is a determination that the turbo counter has a value equal to "6", in step 50 the volume t.b.i. is set to the next factor of 1000, followed by display of the new volume t.b.i. in step 52, incrementing of the turbo counter in step 53 and ending of the interrupt in step 54.

Obviously, numerous modifications and variations of the present invention are possible in light of the above teachings. It is therefore to be understood that within the scope of the appended claims, the invention may be practiced otherwise than as specifically described herein.

What is claimed as new and desired to be secured by Letters Patent of the United States is:

1. An electronically controlled infusion device for controlling fluid to be infused intravenously in the treatment of a patient, comprising:

at least one manually operated control for producing a signal generated by manual operation of the control to set at least one fluid infusion operating parameter; and means for producing an extent of change in said operating parameter for a given extent of movement of said at least one control in dependence upon the speed with which the as least one control is manually operated.

2. A device as claimed in claim 1, comprising:
    plural separate controls for setting the volume to be infused and the flow rate of the fluid to be infused.

3. A device as claimed in claim 2, comprising:
    a dedicated control for each parameter to be set.

4. A device as claimed in claim 1, and wherein said means for producing is responsive to two or more rates of movement, normal or slow movement providing incremental change in the setting of the parameter, or respective parameter, and faster movement causing the setting of said parameter to jump from one predetermined preferred setting to another separated therefrom by a plurality of incremental setting changes.

5. A device as claimed in claim 4, wherein said means for producing is responsive to two rates of movement, normal or slow movement and fast movement, for setting flow rate.

6. A device as claimed in claim 4, and wherein said means for producing is responsive to three rates of movement for setting the volume-to-be-infused.

7. A device as claimed in claim 6, wherein, for setting the volume-to-be-infused said means for producing is responsive to three rates of movement, normal or slow movement causing incremental setting changes; fast movement causing the setting to jump to the next multiple of 100 ml of volume of fluid to be infused, and very fast movement causing the setting to jump to the next adjacent multiple of 1000 ml of volume-to-infused.

8. A device as claimed in claim 1, wherein at least one control comprises a rotary control.

9. A device as claimed in claim 8, wherein said rotary control comprises a digipot.

10. A device as claimed in claim 8, wherein said rotary control comprises a shaft encoder.

* * * * *

UNITED STATES PATENT AND TRADEMARK OFFICE
CERTIFICATE OF CORRECTION

PATENT NO. : 5,366,346
DATED : November 22, 1994
INVENTOR(S) : HAL C. DANBY

It is certified that error appears in the above-indentified patent and that said Letters Patent is hereby corrected as shown below:

Column 6, line 8, change "as" to --at--.

Signed and Sealed this

Fifteenth Day of August, 1995

Attest:

BRUCE LEHMAN

*Attesting Officer*   *Commissioner of Patents and Trademarks*